United States Patent
Martinez et al.

(10) Patent No.: US 9,974,964 B2
(45) Date of Patent: *May 22, 2018

(54) FAULT TOLERANT IMPLANTABLE MEDICAL SYSTEM

(71) Applicant: Medtronic, Inc., Minneapolis, MN (US)

(72) Inventors: Gonzalo Martinez, Mendota Heights, MN (US); Mark T Marshall, Forest Lake, MN (US); Kevin R Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 29 days.

This patent is subject to a terminal disclaimer.

(21) Appl. No.: 14/797,651

(22) Filed: Jul. 13, 2015

(65) Prior Publication Data

US 2015/0314130 A1 Nov. 5, 2015

Related U.S. Application Data

(62) Division of application No. 13/457,884, filed on Apr. 27, 2012, now Pat. No. 9,079,037.

(51) Int. Cl.
*A61N 1/00* (2006.01)
*A61N 1/37* (2006.01)
(Continued)

(52) U.S. Cl.
CPC ............ *A61N 1/3712* (2013.01); *A61N 1/368* (2013.01); *A61N 1/3628* (2013.01); *A61N 1/36592* (2013.01); *A61N 1/3706* (2013.01); *A61N 1/3931* (2013.01); *A61N 1/3937* (2013.01); *A61N 1/3962* (2013.01); *A61B 5/0215* (2013.01); *A61B 2560/0276* (2013.01); *A61N 1/04* (2013.01); *A61N 1/0563* (2013.01); *A61N 2001/0585* (2013.01); *A61N 2001/083* (2013.01)

(58) Field of Classification Search
None
See application file for complete search history.

(56) References Cited

U.S. PATENT DOCUMENTS

| 4,336,811 | A | 6/1982 | Beck et al. |
| 4,760,852 | A | 8/1988 | Lekholm |

(Continued)

OTHER PUBLICATIONS

Hayashi et al., Virtual Electrodes and the Induction of Fibrillation in Langendorff-Perfused Rabbit Ventricles: The role of Intracellular Calcium, Am J Physiol Heart Circ Physiol, Aug. 1, 2008, pp. 2-20, Figures (7 Pages).

(Continued)

*Primary Examiner* — Michael Carey
*Assistant Examiner* — Elizabeth K So

(57) ABSTRACT

The disclosure describes implantable medical systems that respond to occurrence of a lead-related condition by utilizing an elongated coil electrode in defining an alternative pacing therapy vector to maintain optimal drain of an IMD power supply. An exemplary system includes a medical electrical lead having an elongated electrode and an improved sensing and therapy delivery circuitry to provide the alternative pacing therapy vector responsive to the lead-related conditions. The system reconfigures the operation of the sensing and therapy delivery circuitry triggered by the switch to the alternative pacing therapy vector.

20 Claims, 10 Drawing Sheets

(51) Int. Cl.
  *A61N 1/39*   (2006.01)
  *A61N 1/365*  (2006.01)
  *A61N 1/362*  (2006.01)
  *A61N 1/368*  (2006.01)
  *A61N 1/04*   (2006.01)
  *A61N 1/08*   (2006.01)
  *A61B 5/0215* (2006.01)
  *A61N 1/05*   (2006.01)

(56) References Cited

U.S. PATENT DOCUMENTS

| | | | |
|---|---|---|---|
| 5,336,253 | A  | 8/1994  | Gordon et al. |
| 5,342,414 | A  | 8/1994  | Mehra |
| 5,531,782 | A  | 7/1996  | Kroll et al. |
| 5,534,018 | A  | 7/1996  | Wahlstrand et al. |
| 5,534,022 | A  | 7/1996  | Hoffmann et al. |
| 5,654,030 | A  | 8/1997  | Munshi et al. |
| 5,683,443 | A  | 11/1997 | Munshi et al. |
| 5,833,714 | A  | 11/1998 | Loeb |
| 5,849,031 | A  | 12/1998 | Martinez et al. |
| 6,278,897 | B1 | 8/2001  | Rutten et al. |
| 6,327,498 | B1 | 12/2001 | Kroll |
| 6,640,136 | B1 | 10/2003 | Helland et al. |
| 6,978,178 | B2 | 12/2005 | Sommer et al. |
| 7,020,523 | B1 | 3/2006  | Lu et al. |
| 7,186,214 | B2 | 3/2007  | Ness |
| 7,236,828 | B2 | 6/2007  | Casavant et al. |
| 7,239,913 | B2 | 7/2007  | Ding et al. |
| 7,574,259 | B1 | 8/2009  | Pei et al. |
| 7,610,087 | B2 | 10/2009 | Ohman et al. |
| 7,647,108 | B2 | 1/2010  | Freeberg |
| 7,697,985 | B2 | 4/2010  | Kaiser et al. |
| 7,747,320 | B1 | 6/2010  | Kroll et al. |
| 7,848,806 | B1 | 12/2010 | Kroll |
| 7,917,214 | B1 | 3/2011  | Gill et al. |
| 7,953,488 | B2 | 5/2011  | Casavant et al. |
| 2004/0127966 | A1 | 7/2004  | Frericks et al. |
| 2005/0131509 | A1 | 6/2005  | Atanassoska et al. |
| 2005/0221671 | A1 | 10/2005 | Lyu et al. |
| 2005/0256547 | A1 | 11/2005 | Stahmann et al. |
| 2006/0161206 | A1 | 7/2006  | Efimov et al. |
| 2006/0259078 | A1 | 11/2006 | Libbus |
| 2006/0265038 | A1 | 11/2006 | Hagen et al. |
| 2007/0250142 | A1 | 10/2007 | Francis et al. |
| 2008/0004670 | A1 | 1/2008  | McVenes et al. |
| 2008/0275521 | A1 | 11/2008 | Warren et al. |
| 2009/0043351 | A1 | 2/2009  | Sathayee et al. |
| 2010/0198292 | A1 | 8/2010  | Honeck et al. |
| 2011/0319957 | A1 | 12/2011 | Naware et al. |

OTHER PUBLICATIONS

Martinez et al, "Leads for Selective Sensing and Virtual Electrodes", U.S. Appl. No. 12/474,645, filed May 29, 2009, 29 pages.
Marshall, "Lead Recognition for an Implantable Medical System", U.S. Appl. No. 13/457,859, filed Apr. 27, 2012, 33 pages.
P0040444.WOU3 (PCT/US2013/029544) PCT Notification of Transmittal of the International Search Report and the Written Opinion of the International Searching Authority, dated Aug. 20, 2013, 7 pages.

FAULT TOLERANT IMPLANTABLE MEDICAL SYSTEM

CROSS REFERENCE TO RELATED APPLICATION

This application is a divisional of U.S. patent application Ser. No. 13/457,884, filed Apr. 27, 2012 and entitled "FAULT TOLERANT IMPLANTABLE MEDICAL SYSTEM", now U.S. Pat. No. 9,079,037, which is herein incorporated by reference in its entirety. Reference is made to the commonly-assigned U.S. Pat. No. 8,996,111, entitled "LEAD RECOGNITION FOR AN IMPLANTABLE MEDICAL SYSTEM", which is herein incorporated by reference in its entirety.

FIELD

The disclosure relates generally to an implantable medical system. In particular, the disclosure relates to alternate therapy vectors for providing a therapy function in the event of a lead-related condition associated with the lead system.

BACKGROUND

A wide variety of implanted medical devices (IMDs) for delivering a therapy or monitoring a physiologic condition which can employ one or more elongated electrical leads and/or sensors are available. Such IMDs can monitor or deliver therapy to the heart, muscle, nerve, brain, and stomach or other organs. Examples of such IMDs include implantable cardioverter defibrillator devices, which have a pulse generator and one or more electrical leads with one or more electrodes that conduct signals to and receive signals from the patient's heart. These electrical lead(s) and their electrode(s) are placed in or proximate to the organ such that an electrical signal between the electrodes is capable of stimulating the organ. The electrodes may be configured either to deliver a stimulus to the organ, or to detect or sense an intrinsic electrical event associated with the organ.

The leads associated with IMDs typically include a lead body extending between a proximal lead end and a distal lead end that incorporates the one or more exposed electrode or sensor elements located at or near the distal lead end. One or more elongated electrical conductors extend through the lead body from a connector assembly provided at a proximal lead end for connection with associated IMD to the electrode or sensor element located at the distal lead end or along a section of the lead body. Each electrical conductor is typically electrically isolated from other electrical conductors and is encased within an outer sheath insulator, which electrically insulates the lead conductors from body tissue and fluids.

Consideration is taken of various stresses that may be applied to the lead body during an implantation, a lead repositioning procedure, or chronic implanted stresses. For example, continuous flexing of the cardiac lead bodies due to the beating of the heart is an important consideration in maintaining the lead's structural integrity. The effects of lead body damage can progress from an intermittent manifestation to a more continuous effect. In extreme cases, insulation of one or more of the electrical conductors can be breached, causing the conductors to contact one another or body fluids resulting in a low impedance or short circuit. In other cases, a lead conductor can fracture and exhibit an intermittent or continuous open circuit resulting in an intermittent or continuous high impedance. Such lead issues resulting in short or open circuits, for example, can be referred to, for simplicity, as "lead-related conditions."

In the case of cardiac leads, the ability to sense cardiac activity conditions accurately through a lead can be impaired by these lead-related conditions. Complete lead breakage impedes any sensing functions while lead conductor fractures or intermittent contact can demonstrate electrical noise that interferes with accurate sensing. During cardiac pacing or defibrillation, lead-related conditions can reduce the effectiveness of a pacing or defibrillation pulse or therapy to below that which is sufficient to pace or defibrillate the heart.

It is generally desirable to provide mechanisms to sustain therapy delivery in the event of a lead-related condition.

SUMMARY

Generally, the present disclosure addresses the need to provide back-up pacing and sensing vectors in response to a lead-related condition impacting one or more components of an implantable medical system, such as a medical electrical lead. The ability to sustain therapy delivery in response to the occurrence of the lead-related condition is based in part on the viability of the remaining therapy vectors. The remaining therapy vectors are defined by the electrode-conductor sets that are unaffected by the lead-related condition.

In an embodiment, an implantable medical system for sustaining therapy includes a lead having a first electrode and an alternate electrode wherein the system switches delivery of therapy from the first electrode to the alternate electrode in response to a lead-related condition. The system may further include an oversense reduction module that reconfigures the therapy to be delivered triggered by the switch from the first electrode to the alternate electrode.

In another aspect, a sensing function of the implantable medical system is reconfigured in response to occurrence of the lead-related condition. In one embodiment, the implantable medical system includes an oversense reduction module for processing of signals sensed through the alternate electrode.

According to another illustrative embodiment, a method for delivering therapy includes providing a therapy through a first electrode; reconfiguring the therapy in response to a detected lead-related condition and providing the therapy through a distal portion of an alternate electrode. In another embodiment, the method may include reconfiguration of a sensing function in response to the occurrence of the lead-related condition for sensing through an alternate electrode.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

The present disclosure can be practiced in the context of the implantable medical systems described herein. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

An implantable cardiac system is used to sense electrical activity indicating events occurring in one or more heart chamber of a patient. The sensed electrical signals are transmitted in a raw form through one or more lead(s) for processing by an implantable medical device (IMD) of the cardiac system. The sensed electrical activity is processed by the IMD and the results of the processing are used for controlling therapy delivery by the cardiac system. One aspect of such cardiac systems is the difficulty of sustaining therapy in the presence of a condition impacting the lead's performance.

Generally, lead-related conditions may be understood to refer to any condition prohibiting or frustrating use of the lead in the desired manner during normal operation of the cardiac rhythm management system. In addition to those already discussed, these conditions also include but are not limited to parameters associated with physical conditions of the lead such as sensed noise, lead impedance outside a predetermined range, capture failure, capture amplitude voltage outside a predetermined range, intrinsic amplitude outside a predetermined range, failure to detect an expected event, and an electrical hardware failure.

Figure 1:
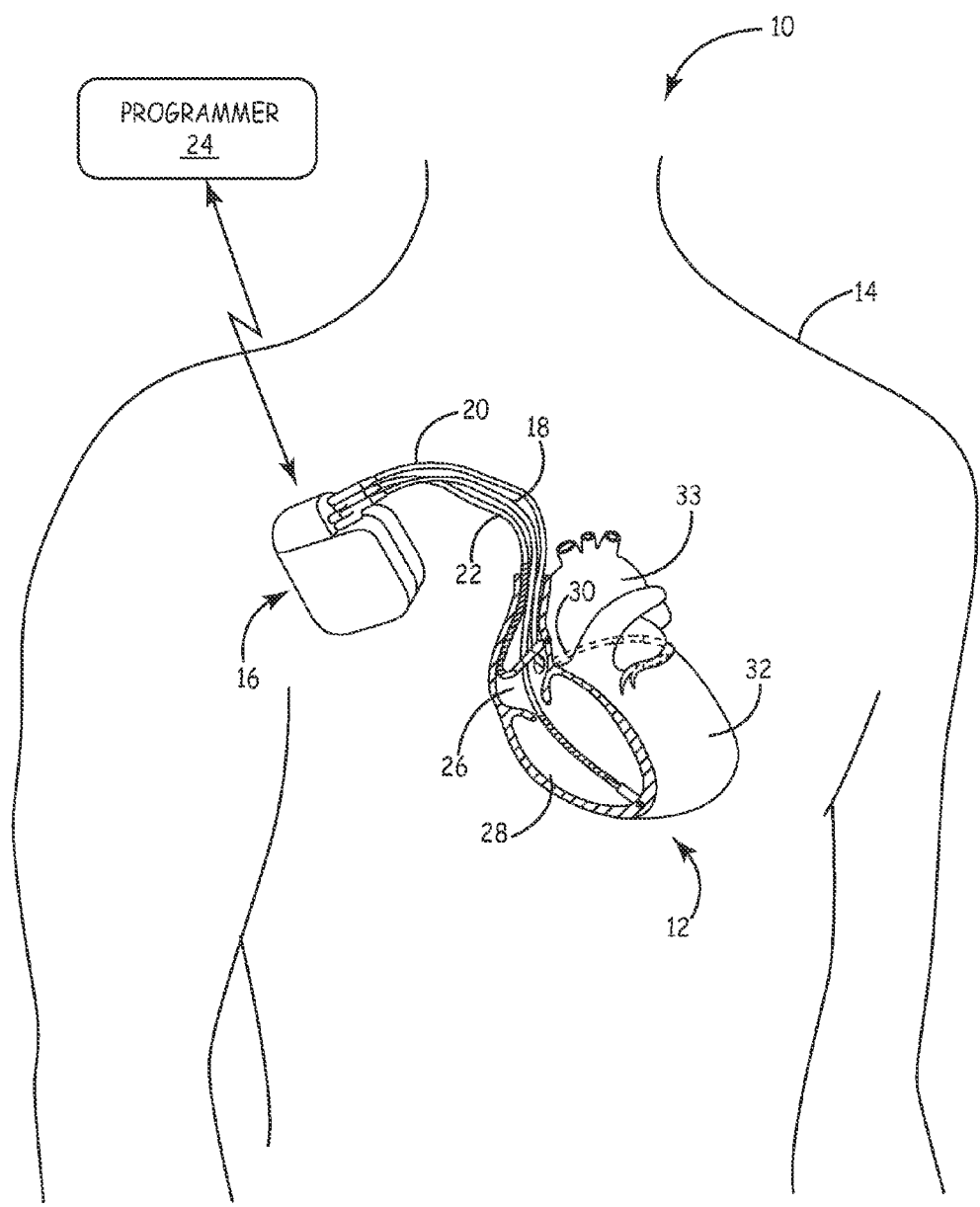
FIG. 1 is an exemplary implantable therapy system that may be used to provide therapy to heart of a patient is described.

Referring to FIG. 1, an exemplary implantable cardiac system that may be used to provide therapy to heart 12 of patient 14 is described. Patient 14 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Each of leads 18, 20 and 22 may carry one or a set of electrodes. The electrode may extend about the circumference of each of leads 18, 20, and 22 and is positioned at a respective axial position along the length of each of the lead 18, 20, and 22.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. In alternative embodiments, the LV lead 20 may also be introduced into the left ventricle through the septal wall. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a patient, physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation shocks, select waveforms for the defibrillation shock, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
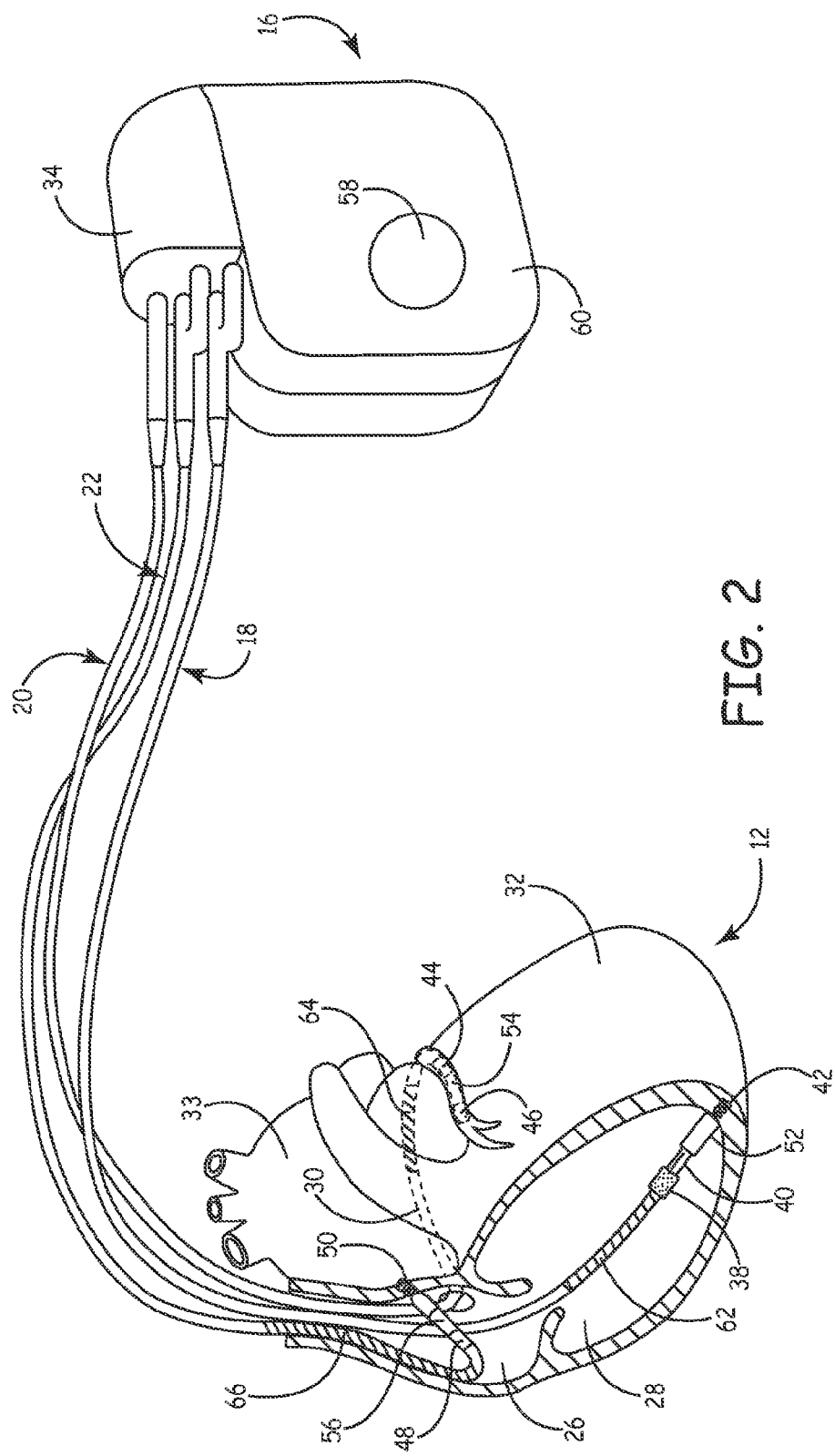
FIG. 2 is a conceptual diagram illustrating an implantable medical device and leads of a therapy system in greater detail.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules of IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors, or parallel cable conductors in a multi-lumen lead body or co-radial conductors all of which are separated from one another by tubular insulative sheaths. In the illustrated example, a pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. In FIG. 2, pressure sensor 38 is disposed in right ventricle 28. Pressure sensor 30 may respond to an absolute pressure inside right ventricle 28, and may be, for example, a capacitive or piezoelectric absolute pressure sensor. In other examples, pressure sensor 30 may be positioned within other regions of heart 12 and may monitor pressure within one or more of the other regions of heart 12, or may be positioned elsewhere within or proximate to the cardiovascular system of patient 14 to monitor cardiovascular pressure associated with mechanical contraction of the heart.

Among the electrodes, some of the electrodes may be provided in the form of coiled electrodes that form a helix, while other electrodes may be provided in different forms. Further, some of the electrodes may be provided in the form of tubular electrode sub-assemblies that can be pre-fabricated and positioned over the body of leads 18, 20, 22, where they are attached and where electrical connections with conductive elements within the leads 18, 20, 22 can be made. For example, electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define one or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As is known in the art, housing 60 may enclose a stimulation generator that generates cardiac pacing pulses and defibrillation or cardioversion shocks, as well as a sensing module for monitoring the patient's heart rhythm.

Leads 18, 20, 22 also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion therapy to heart 12. Additionally, unipolar pacing and/or sensing may be implemented, for example, using one of the coil electrodes 62, 64, 66 referenced to the can electrode 58 in accordance with embodiments of this disclosure. The electrodes 62, 64, 66 may be fabricated as will be described in more detail in FIG. 6.

Pressure sensor 38 may be coupled to one or more coiled conductors within lead 18. In FIG. 2, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 22 in other examples, or to a lead other than leads 18, 20, 22 carrying stimulation and sense electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 33. Other examples of therapy systems may include a single lead that extends from IMD 16 into right atrium 26 or right ventricle 28, or two leads that extend into a respective one of the right ventricle 26 and right atrium 28. An example of this type of therapy system is shown in FIG. 3.

Figure 3:
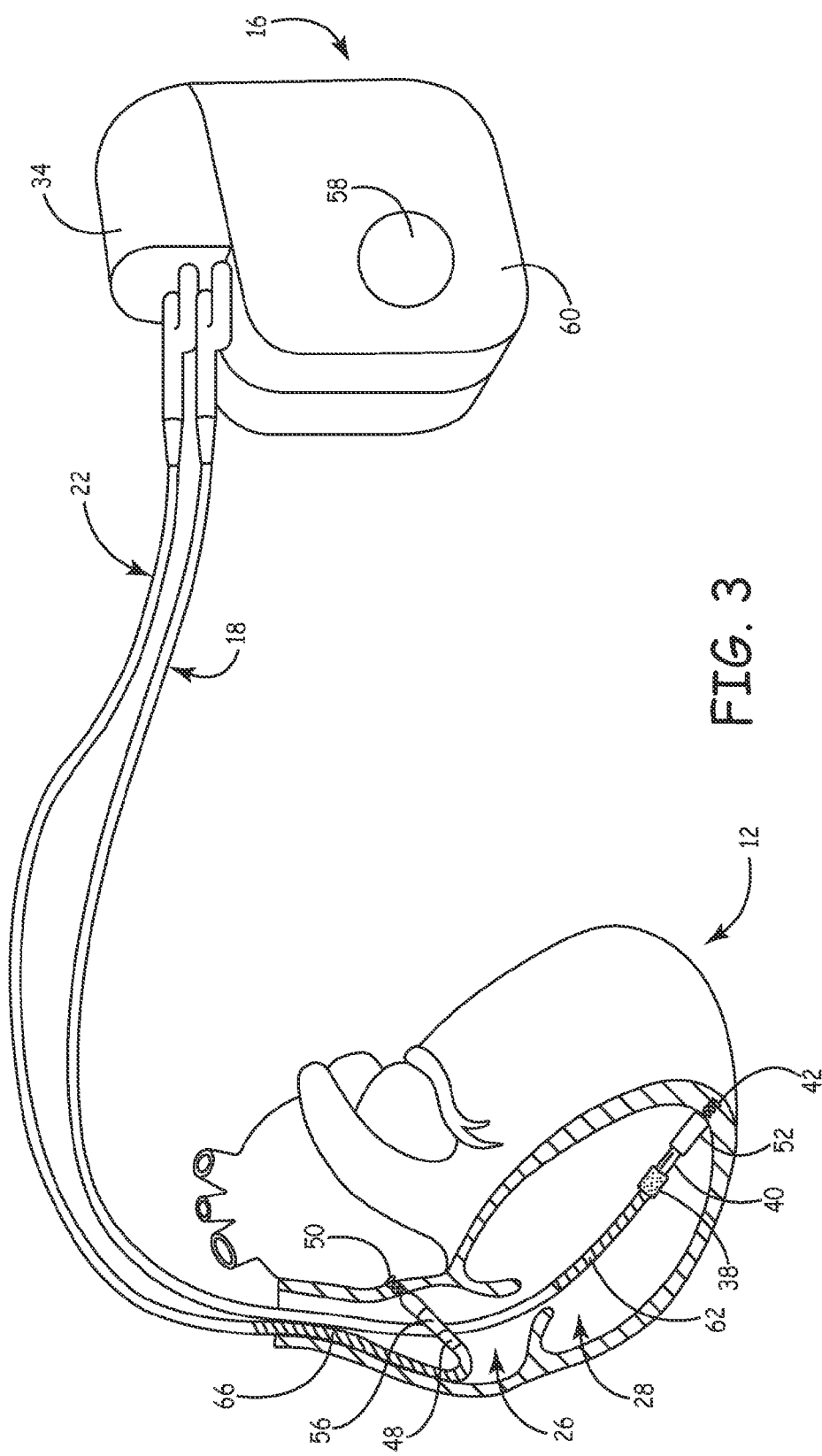
FIG. 3 is a conceptual diagram illustrating another example of therapy system, which is similar to therapy system of FIGS. 1-2.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12.

Figure 4:
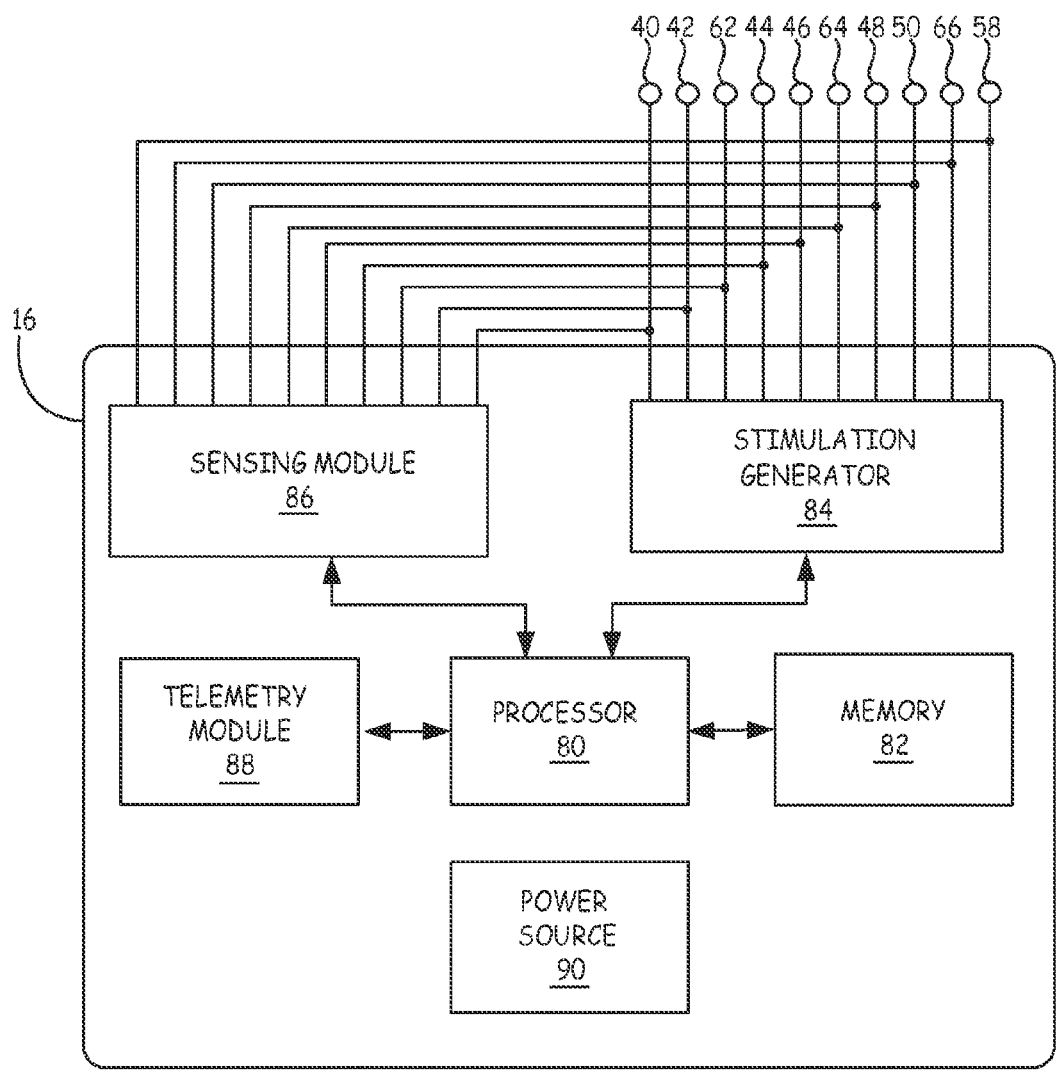
FIG. 4 is a functional block diagram of one example configuration of an implantable medical device.

FIG. 4 is a functional block diagram of one example configuration of IMD 16, which includes processor 80, memory 82, stimulation generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 controls stimulation generator 84 to deliver stimulation therapy to heart 12 according to a selected one or more of therapy programs, which may be stored in memory 82. Specifically, processor 44 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Stimulation generator 84 is configured to generate and deliver electrical stimulation therapy to heart 12. For example, stimulation generator 84 may deliver defibrillation shocks to heart 12 via at least two electrodes 58, 62, 64, 66. In some examples, stimulation generator 84 delivers pacing, cardioversion, or defibrillation stimulation in the form of electrical pulses. In other examples, stimulation generator may deliver one or more of these types of stimulation in the form of other signals, such as sine waves, square waves, or other substantially continuous time signals. In accordance with embodiments of this disclosure, stimulation generator 84 may deliver pacing pulses via elongate electrodes 62, 64, and 66.

Stimulation generator 84 may include a switch module and processor 80 may use the switch module to select, e.g., via a data/address bus, which of the available electrodes are used to deliver defibrillation shocks or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12, e.g., via electrocardiogram (ECG) signals. Sensing module 86 may also include a switch module to select which of the available electrodes are used to sense the heart activity. As will be described in more detail elsewhere, the sensing module 86 may employ oversense reduction circuitry (FIG. 6) for signals sensed via electrodes 62, 64, or 66. In some examples, processor 80 may select the electrodes that function as sense electrodes via the switch module within sensing module 86, e.g., by providing signals via a data/address bus. In some examples, sensing module 86 includes one or more sensing channels, each of which may comprise an amplifier. In response to the signals from processor 80, the switch module of sensing module 86 may couple the outputs from the selected electrodes to one of the sensing channels.

In some examples, sensing module 86 may include one or more amplifiers that receive signals from one or more of the electrodes. In some examples, the amplifiers may take the form of an automatic gain controlled amplifier that provides an adjustable sensing threshold as a function of the measured P-wave or R-wave amplitude of the heart rhythm. Examples of such amplifiers are described in U.S. Pat. No. 5,117,824 to Keimel et al., which issued on Jun. 2, 1992 and is entitled, "Apparatus for Monitoring Electrical Physiologic Signals," and is incorporated herein by reference in its entirety. Furthermore, in some examples, one or more of the sensing channels of sensing module 86 may be selectively coupled to housing electrode 58, with elongated electrodes 62, 64, or 66, e.g., for unipolar sensing of R-waves or P-waves in response to lead-related conditions.

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

In general, the ability to sustain therapy delivery in response to a lead-related condition is limited by the availability of alternate therapy vectors that are defined by the remaining, viable, electrode combinations. For example, some cardiac systems have been provided with redundant electrodes or leads and such systems may revert to an alternate electrode combination on the redundant lead for backup therapy functionality. However, providing redundancy in the lead system may not be feasible or desirable.

Figure 5A:
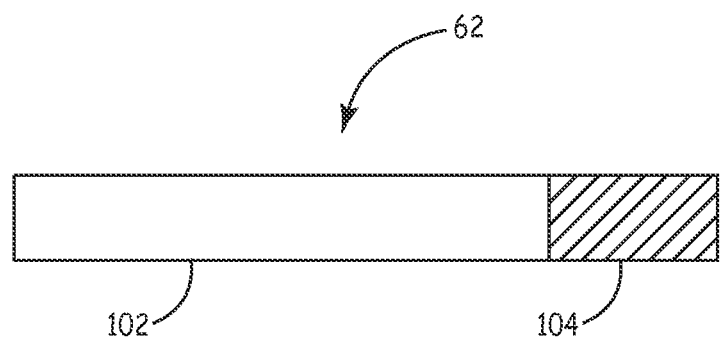
FIGS. 5A-B depict alternate embodiments of an elongated electrode that provides an alternate pacing vector in the event of occurrence of a lead-related condition.
Figure 5B:
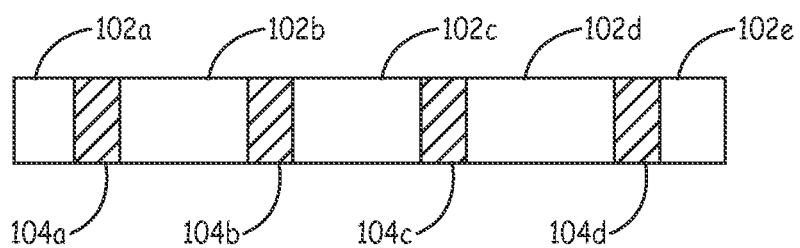

FIGS. 5A-B depict alternate embodiments of an elongated electrode that provides an alternate pacing vector in the event of occurrence of a lead-related condition. The elongated electrode includes a first section and a second section with the first section having a first material that is different from a second material of the second. The elongated electrode defines a first vector for providing cardioversion and/or defibrillation therapy and a second vector for alternative pacing therapy. The construction of the elongated electrode first and second sections with different materials facilitates selective pacing and sensing making the vector defined by the elongated electrode and the housing electrode amenable as an alternative pacing vector.

The present inventors have noted the need to provide viable alternative pacing vectors in the presence of lead-related conditions without increasing the complexity or size of the lead systems. In particular, the construction of conventional elongated (coil) electrodes and the conductors coupling these electrodes to the IMD renders them less susceptible to being compromised by the stresses that are applied to the lead system. For example, the conductor(s) associated with the elongated electrode is constructed to enable coupling of defibrillation energy. The defibrillation conductors are designed to withstand a greater amount of stress in comparative relation to the conductors associated with pacing electrodes. Yet, such coil electrodes are generally unsuitable as an alternative for providing a fault tolerant pacing vector. In comparison to ring and tip electrodes, the coil electrodes generally have a much larger surface area. For example, the surface area of a coil electrode may range from 50 to 100 times greater than the ring and tip electrode. Owing to the larger surface area, the electric field is weakened, relative to the smaller surface area of the ring or tip electrodes, because the current is spread over the entire surface area. The larger surface area of the coil electrode makes it impractical for delivering pacing pulses because it requires that relatively greater current be delivered to achieve capture in comparison to the energy that is typically delivered through a tip or ring electrode for the same therapeutic function. In most instances, the requirement for increased current consumption owing to the greater coil electrode surface area would at worst result in failure to capture the heart and at best would result in enhanced current drain thereby exhausting the battery resources within a much shorter time frame in comparison to ring and tip electrodes.

In FIG. 5A, the elongated electrode 62 depicted includes a first section 102 that is located proximal to a distally located second section 104. The elongated electrodes 64 and 66 may also be constructed similar to elongated electrode 62. In one embodiment, the entire surface area of elongated electrode 62 includes a first material and the distal, second, section 104 is further formed with a second material that encapsulates the first material over that portion. The resulting electrode 62 therefore has the exposed surface area of the first portion 102 having the first material while the surface area of the exposed second portion 104 has the second material.

Unlike the conventional coil electrodes, the elongated electrode 62 may be formed such that only a selected one of the first and second sections conducts electric currents that are below a specified threshold. The material of the selected section may be one that permits conduction of current that has a value at or below a certain threshold while the material of the unselected section would perform as an insulator when such currents are delivered. Both sections would, however, be conductive for currents exceeding the threshold. Such an electrode configuration enables the electric field of certain magnitude, for example pacing pulses, to be focused only on the selected first or second section. In other words, an optimal electric field sufficient for providing pacing therapy that is applied to the electrode would be focused only on the surface area of the conductive region of the elongated electrode.

The proportions of the proximal portion 102 to the distal portion 104 are chosen to facilitate delivery of pacing stimulus through the distal portion 104 but to permit delivery of defibrillation therapy through both the proximal portion 102 and the distal portion 104. The proportions of the distal to proximal portions are selected based on the total surface area of a given electrode 62 that delivers a defined amount of energy. For example, a typical elongated electrode 62 having a total surface area of approximately 200 mm$^2$ will have the distal portion 104 occupying about 20% of the total surface area or about 40 mm$^2$. In another example, an elongated electrode with a surface area of about 400 mm$^2$ will have include a proximal portion 102 that occupies about 90% of the total electrode surface area and a distal portion with a surface area of about 40 mm$^2$. In other words, for the typical elongated electrode having a surface area ranging between 200 to 600 mm$^2$, the distal portion will range from about 20 to 40 mm$^2$, respectively. In other embodiments, the relative surface areas of the proximal portion to distal portion may be expressed as a ratio ranging from about 10:90 to about 99:1, respectively.

FIG. 5B illustrates an alternative embodiment of an elongated electrode. In the alternative embodiment, the electrode 62b may be constructed such that the second section is segmented into multiple portions that are interspersed between the first section. As such, rather than having a continuous first section coupled to a continuous second section as is illustrated in the embodiment of FIG. 5A, the alternate embodiment of FIG. 5B illustrates the electrode 62 formed with the first section 102 being distributed over the first section. The resulting configuration is the electrode 62b that has multiple second sections 104a, 104b, 104c, and 104d that are interspersed between multiple first sections 102a, 102b, 102c, 102d, and 102e. Such an elongated electrode configuration may be beneficial in providing an elongated electrode that provides closer contact with cardiac tissue for example when the electrode is bent towards the blood pool. For example, the surface area of the second section 104 may be divided into four sections 104a-d, which combine to equate to the total surface area of the distal portion 104 and conversely, the sections 102a-e all equate to the total surface area of the proximal portion 102.

Examples of the first material include (used in their native oxide form or surface treated, i.e., anodized, doped, ion implanted, reactive sputtered, or any other chemical or physical treatment of the surface) include valve metals such as titanium, tungsten, chromium, aluminum, zirconium, hafnium, zinc, vanadium, niobium, tantalum, bismuth, antimony, and also include oxides, mixtures, and alloys thereof. Other materials that can be used include diamond, diamond-like-carbon (DLC) and other nanostructured materials, metal oxides or mixtures of metal oxides, nitrides, carbides, semiconductors, conductive ceramics and ceramic oxides, conductive glasses, conductive polymers, gels, polymer-metal composites, and ceramic or glass composites. These various materials may substitute for each other or may be used in combination as the first material. The materials may be further provided with an oxide coating (e.g., tantalum pentoxide "$Ta_2O_5$") which imparts useful properties such as corrosion resistance, EMI (electromagnetic interference) isolation and electrical resistance.

Examples of the second material include good conductor metals such as platinum, rhenium, vanadium, zirconium, palladium, iridium, titanium, niobium, tantalum, ruthenium, silver, molybdenum, silver chloride, cobalt, chromium, tungsten, magnesium, manganese, and their alloys. Examples of the second material also include conductive diamonds, nanotubes, and other nanostructured materials, nonmetals such as carbon, nitrides, conductive polymers, conductive ceramics and composites made of combinations of these materials, including combinations of metals and nonmetals. The nonmetals may also be combined with the metals of the second material to form the second metal.

Figure 6:
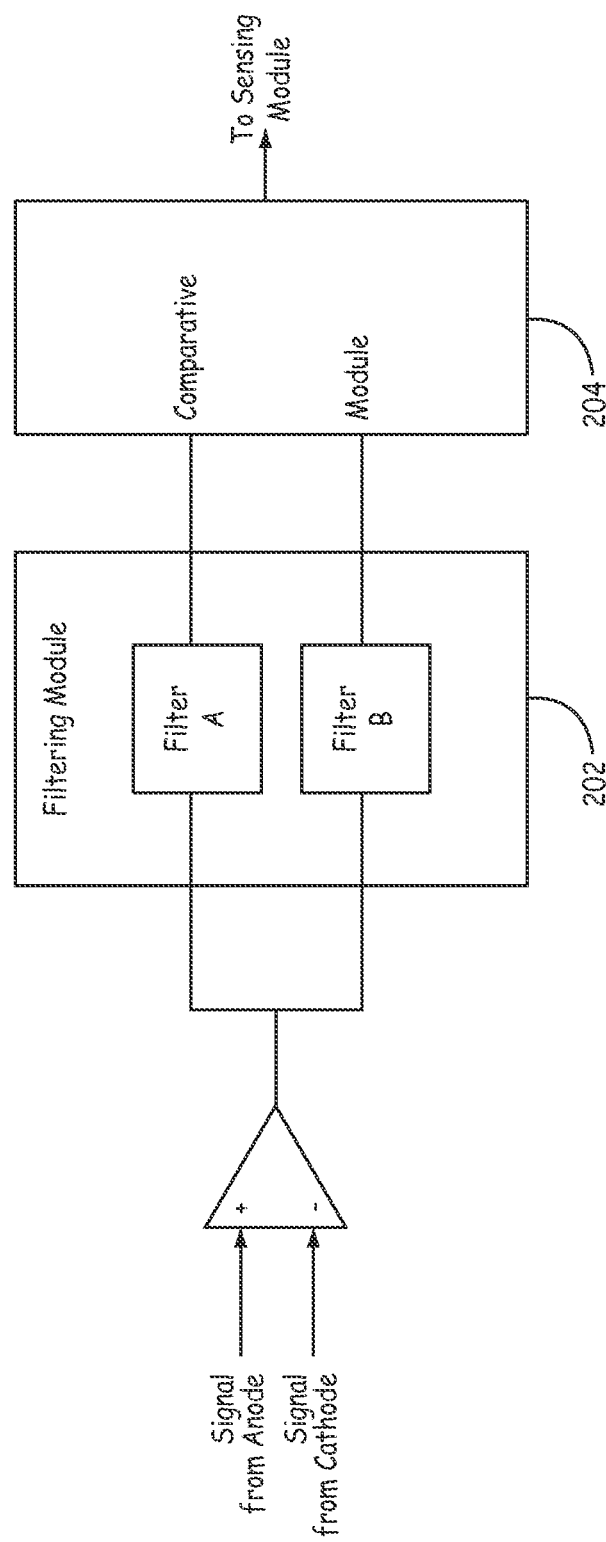
FIG. 6 illustrates a block diagram of oversense reduction module for sensing cardiac events in accordance with an embodiment of the disclosure.

FIG. 6 illustrates a block diagram of oversense reduction module 200 for sensing cardiac events in accordance with an embodiment of the disclosure. Module 200 may be incorporated or coupled to conventional sense circuitry such as sensing module 86 of IMD 16. The oversense reduction module 200 deconstructs the composite signal into the individual first and second constituent signals that are received from the proximal and distal portions of the elongated electrode in response to a cardiac event. The deconstruction of the sensed signal with module 200 compensates for the difference in the propagation of a single event sensed by both the proximal and distal portions of the elongated electrode 62, for example.

The oversense reduction module 200 includes a filtering module 202 that isolates the two constituent signals of the composite signal. The filtering characteristics of filtering module 202 may be selected based on the material properties for the distal and proximal portions of elongated electrode 62. In particular, the module 202 includes a plurality of band pass filters that are tuned to deconstruct the composite signal into its constituent signals. For example, in the embodiment of the electrode having two portions, i.e., a distal and a proximal portion, the module 202 will have two band pass filters that will each output the signals sensed through the distal and proximal portions. The input of these band pass filters is the composite signal sensed by the elongated electrode 62. Because the characteristics of the materials are known, each of the band pass filters can be designed to pass through the frequency associated with one material while attenuating the frequency associated with the other material. The raw signal from the distal portion may be provided to the sense circuitry in accordance with conventional sensed signal processing.

An additional aspect of the oversense reduction module 200 may be a comparative analysis of the deconstructed signals. This analysis may be performed in comparative module 204. The comparative module 204 may utilize an algorithm to determine whether the two constituent signals that are obtained from the composite signal sensed via the elongated electrode actually represent a single cardiac event. The comparative module 204 may employ predetermined criteria to determine the instances in which to evaluate signals that may be suspected to represent the same event but otherwise appear as discrete signals due to disparities owing to the sensing by the elongated electrode. Such predetermined criteria may include the interval between the constituent signals of the composite signal. For example, if the interval between the signals is greater than 100 milliseconds, the comparative module 204 will deem the composite signal as requiring further evaluation. In one embodiment, the algorithm may evaluate the suspect signals by comparing their morphologies to determine whether there is a correlation between the signals. In response to determining that there is a correlation, one of the two signals such as the proximal signal may be discarded from further processing. For example, the lagging signal may be discarded as being a redundant signal. In response to ascertaining that the signal is indeed a potential cardiac event, the sensed signal is propagated to the sense circuit for further processing.

Figure 7:
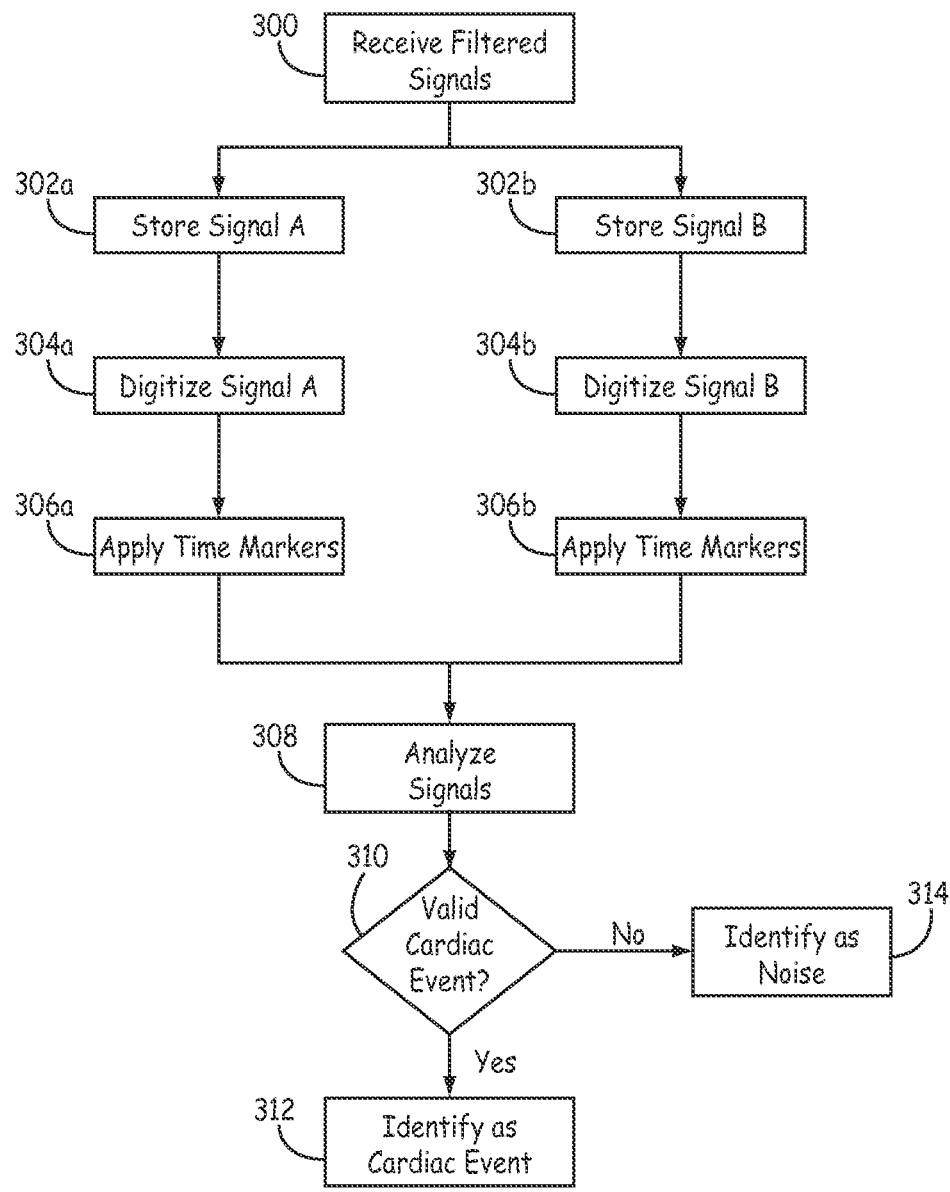
FIG. 7 illustrates a flowchart that represents one embodiment of an algorithm that may be implemented in a comparative module for evaluation of the signals received from the elongated electrode.

FIG. 7 illustrates a flowchart that represents one embodiment of an algorithm that may be implemented in comparative module 204 for evaluation of the signals received from the elongated electrode. Although this example embodiment is described with reference to the electrode 62 illustrated in FIG. 5A, the concepts can easily be applied to the signals received from the segments of first and second sections of the electrode of FIG. 5B. As previously discussed, filtering is applied to isolate a signal A that represents the signal received from the proximal portion 102 of the elongated electrode from a signal B representing the signal received from the distal portion 104 of the elongated electrode. The signal A may be stored in a memory location at step 302a. Additionally, the signal B may be stored in a memory location at step 302b. The signals A and B may be converted from their raw analog form into digital signals at steps 304a and 304b, respectively.

The inventors have observed that one resultant effect of sensing physiologic signals via the proximal and distal portions is that the signal A exhibits a time shift relative to signal B. To account for the time shift, time markers may be applied at steps 306a, 306b to the signals A and B, respectively, to accurately depict the interval between the signals.

The signals may subsequently be analyzed at 308 to determine whether the received composite signal is indicative of a cardiac event. For example, signals A and B may be compared to determine whether they are identical. The comparison may utilize the time markers to accurately overlay the signals. In another example, one or both signals may be compared to a reference signal to determine whether the received signal is consistent with a cardiac event. Such a reference signal may be the morphology of the patient's known cardiac waveform, for example. Based on the results of the analysis, the comparative module 204 determines (310) whether the received signals are either representative of a potential sensed event or a noise signal. The signal is subsequently identified as either a sensed event (312) or a noise signal (314).

Figure 8:
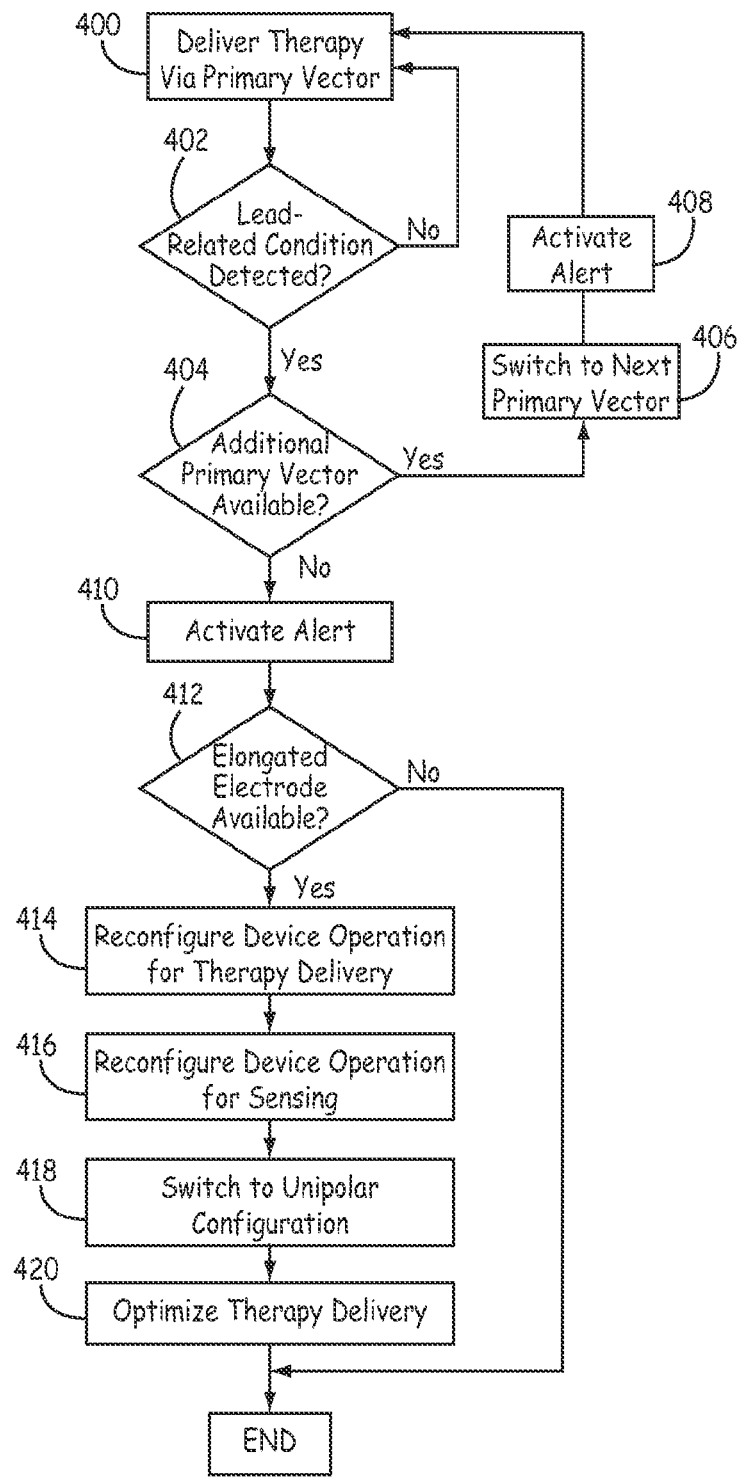
FIG. 8 illustrates a process for sustaining therapy delivery in response to occurrence of a lead-related condition according to one embodiment of the disclosure.

The flowchart of FIG. 8 illustrates a process for sustaining therapy delivery in response to occurrence of a lead-related condition according to one embodiment of the disclosure. For ease of discussion and without intending to be limiting, the process is described as being embodied in the system 10. Therapy delivery is sustained utilizing an electrode combination that includes an elongated electrode to define an alternate pacing vector upon the occurrence of a lead-related condition.

Typically, pacing energy is delivered to the heart tissue via a cathode electrode(s) at one or more pacing sites, with a return path provided via an anode electrode(s). If capture occurs, the energy injected at the cathode electrode site creates a propagating wavefront of depolarization which may combine with other depolarization wavefronts to trigger a contraction of the cardiac muscle. The cathode and anode electrode combination that delivers the pacing energy defines the pacing vector used for pacing. The position of the cathode relative to cardiac tissue can be used to define an electrode combination and/or a pacing site.

The process utilizes a primary vector for delivery of the pacing therapy to the patient (400). The primary vector is defined for an "electrode combination," where the term "electrode combination" denotes that at least one cathode electrode and at least one anode electrode are used. For example, multiple electrodes that are electrically connected may be used as the anode and/or multiple electrodes that are electrically connected may be used as the cathode and the pacing pulses are delivered via the cathode/anode electrode combinations.

Examples of such pacing electrodes are the ring and tip electrodes, such as 40, 42, 44, 46, 48 and 50. Such electrodes for delivery of pacing pulses are generally constructed with dimensions to define an optimal surface area that enables delivery of sufficiently high current density associated with the low voltage levels characterized by pacing pulses. One or more vectors, defined via a combination of any one or more of the ring or tip electrodes may be established as a primary vector(s) for delivery of pacing therapy. In the event of multiple cathode/anode electrode combinations, a hierarchical relationship may be established between the two or more primary vectors. The relationship may take into account such factors as the location of each electrode vis-à-vis efficacy of therapy delivered through the electrode, the likelihood of phrenic nerve stimulation, capture threshold and other factors that may be measured when evaluating pacing efficacy.

During the course of operation of therapy system 10, the lead system is monitored to identify an occurrence of a lead-related condition associated with the primary vector (402). As previously noted, lead-related conditions are typically associated with the lead conductor(s) and breaches in insulation but may also extend to the electrode and electrode-to-conductor interface. Several approaches for monitoring lead-related conditions have been described in the art and this disclosure is not limited to any given monitoring technique; any detection technique may be utilized consistent with the embodiments of this disclosure. As a non-limiting example, such techniques include lead impedance, capture management and capture threshold amplitude, phrenic nerve thresholds, and R-wave amplitudes.

In response to detecting a lead-related condition, the process determines whether another primary vector is available for continued therapy delivery (404). Such an additional primary vector may be defined by a different set of ring and/or tip electrodes 40, 42, 44, 46, 48 and 50. In determining whether an additional primary vector is available, the therapy system will also assess whether the vector is viable. If the additional primary vector is available and viable, the therapy system may switch to that primary vector in response to the detected lead-related condition (406). The system may also activate an alert to inform the patient and/or clinician of the detected lead-related condition and the action that has been taken (408). However, if there is no remaining primary vector that would be appropriate for providing a suitable electrode combination, an alarm may be activated to alert the patient and/or clinician (410). The alerts generated at steps 408 and 410 may be different. For instance, a lower level alert may be generated at 408 while a higher level is issued at 410.

In accordance with embodiments of the disclosure, the process assesses whether the lead system includes an elongated electrode (412). One embodiment for assessment of the availability of the elongated electrode is described with reference to FIGS. 9 and 10. Another example for the identification is illustrated in U.S. Pat. No. 5,534,018 which is incorporated by reference herein in relevant part. The elongated electrode represents an alternative pacing vector which may sustain therapy delivery albeit with a lower cardiac efficacy in comparison to the primary vector(s). Nevertheless, the alternative pacing vector may ensure that life sustaining therapy is still provided to the patient until such time when a lead replacement may be performed to replace the ring or tip electrodes.

If an alternate electrode is available, the process reconfigures the implantable device for therapy delivery via the alternate vector (414). Unlike switching between the plurality of primary vectors, it is contemplated that the operation of therapy system 10 is reconfigured if the electrode combination includes the elongated electrode. Among other things, the reconfiguration of the operation of system 10 compensates for the differences in construction of the elongated electrode in comparison to the ring and tip electrode. When utilizing the elongated electrode for pacing, the electric fields for pacing are focused on the second section (or distal portion) of the electrode thereby reducing the pacing threshold as compared to pacing with the entire surface area of the elongated electrode. As discussed elsewhere in this disclosure, the elongated electrode includes first and second sections each having a different material. Owing to the markedly different properties of the two materials the electric fields of the therapy delivered through the elongated electrode may be configured to be delivered only through the distal portion. In some embodiments, the pacing pulse waveform generator may be reconfigured to define a stimulation pulse waveform that is suitable for delivery of pacing pulses through the second section of the electrode. In any event, the therapy is reconfigured to enable therapy delivery through only the second section which reduces the current drain for effective therapy delivery.

The inventors have also observed that the timing relationship for sensing of electrical activity representing a cardiac event may be offset when sensing functionality is switched to the elongated electrode. In other words, a single signal representing a cardiac event that is detected by the elongated electrode may be received by the sense signal as a composite signal having two different components. The first component is the signal received at the distal portion and the second component is the signal received at the proximal portion.

Because of the lack of a 1 to 1 correspondence between the signal sensed at the distal portion and the sensed at the proximal portion, the sense circuit may inadvertently interpret the composite signal as two differently occurring events. To avoid the erroneous interpretation of the composite signal, the IMD may reconfigure the sense circuit in response to switching the electrode configuration from the first electrode to the alternate electrode (416). In another embodiment, reconfiguration may include adjusting the gain parameter of the sensing circuit to prevent or significantly reduce sensing of noise signals that may result in an erroneous determination of a cardiac event.

With continued reference to FIG. 8, the process may, in an embodiment, switch the therapy modes or pacing configuration of the electrodes for optimal therapy delivery (418). For example, operation of system 10 may be switched to a ventricular inhibited (VDD) pacing mode or to a unipolar pacing configuration utilizing the elongated electrode and the can electrode. The process further switches the cathode selection from the primary (ring or tip) electrode to the elongated electrode. As a result of the operational switch, the therapy energy generated by the device is delivered via the vector defined by elongated electrode (cathode) and the can electrode (anode).

In other embodiments, the process may further include adjustments to the pacing parameters to optimize therapy delivery under the alternate vector (420). In one example, a pacing (capture) threshold test may be performed to re-determine the capture threshold to facilitate optimal power consumption. In another example, the programmed safety margin may be assessed to determine whether appropriate capture occurs for the alternate vector. In the event that the capture threshold and/or the safety margin are inadequate, the process may adjust these parameters to ensure capture for therapy delivered under the alternate vector.

Upon completion of the system 10 reconfiguration, the process proceeds to deliver therapy via the alternative pacing vector defined by the elongated electrode and the can electrode.

Figure 9:
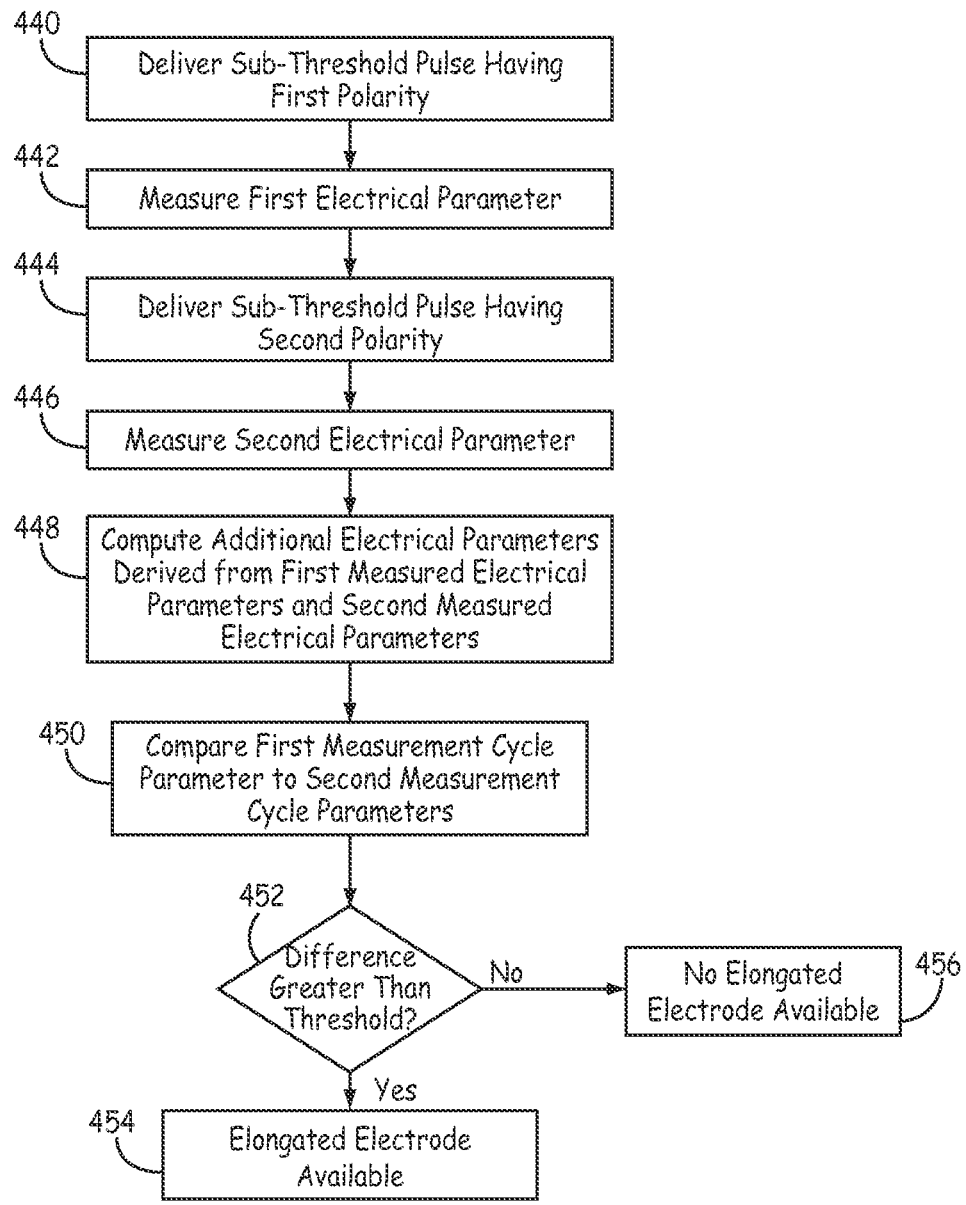
FIG. 9 illustrates a flow chart in accordance with an embodiment for assessing whether a lead system includes an elongate electrode of the type contemplated in this disclosure.

FIG. 9 illustrates a flow chart in accordance with an embodiment for assessing whether a lead system includes an elongate electrode of the type contemplated in this disclosure. Specifically, the elongate electrode is one such as that discussed in FIGS. 5A-B that has a first section having a first material and a second section having a second material.

As noted in FIG. 8 above (412), a determination may be made of whether an elongate electrode such as electrode 62 is available. In the assessment of FIG. 9, the determination is accomplished through the delivery of sub-threshold voltage pulses of opposite polarities on the lead conductive pathway such that the impedances observed following delivery of the respective opposite polarity pulses can be evaluated.

Figure 10:
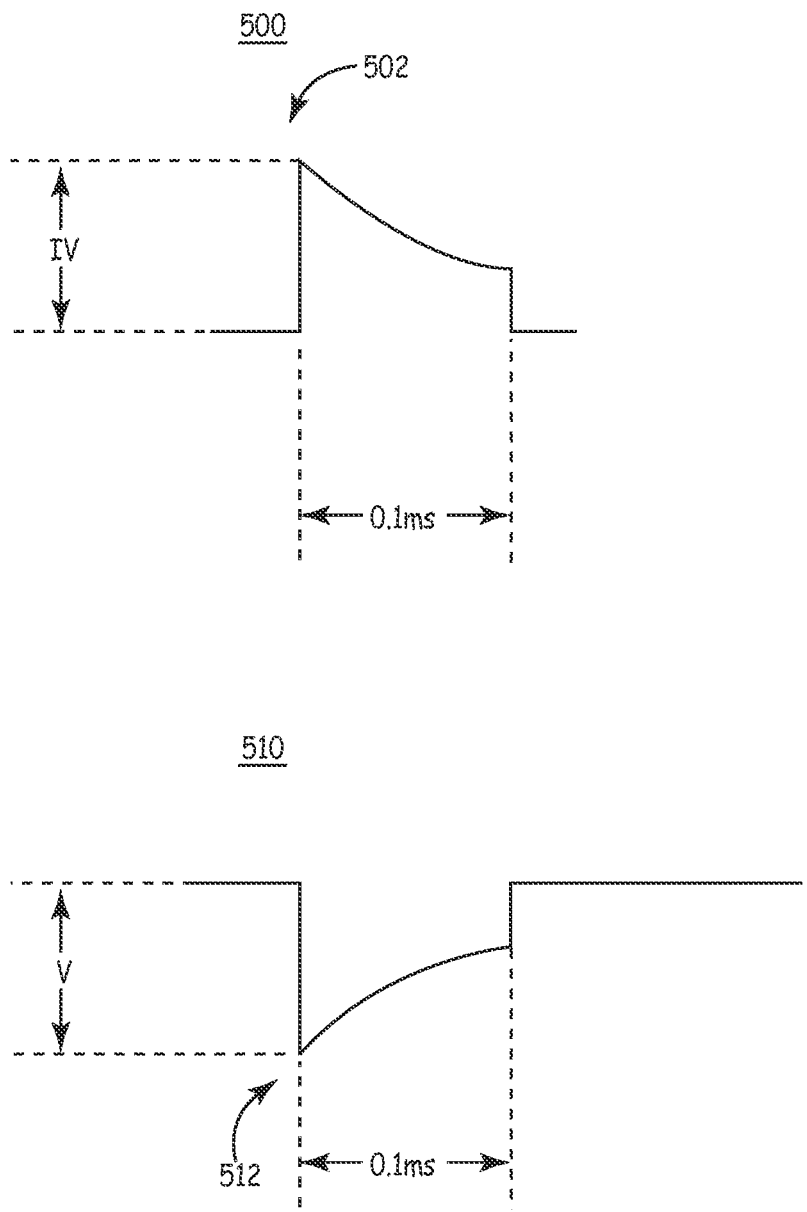
FIG. 10 depicts one example of the sub-threshold voltage pulse waveform generated by a stimulation generator of the implantable medical device.

To this end, stimulation generator 84 (FIG. 4) includes circuitry for generating the small sub-threshold voltage pulses, which are periodically and sequentially issued along the conductive pathway of the lead. An illustration of one example of the sub-threshold voltage pulse waveform generated by stimulation generator 84 is shown in FIG. 10. As shown in FIG. 10, sub-threshold voltage pulse 500, 510 are biphasic pulses. Sub-threshold pulse 500 has a leading positive phase 502 while sub-threshold pulse 510 has a leading negative phase 512. Both sub-threshold pulses 500, 502 have a peak amplitude of about one (1) volt, and a duration of approximately 0.1 milliseconds. It is believed that the implementation of circuitry for generating pulses such as depicted in FIG. 10 would be a matter of routine engineering to those of ordinary skill in the art; therefore, the details of such circuitry will not be described further herein.

With continued reference to FIG. 9, a sub-threshold voltage pulse of a first polarity is delivered through the conductive pathway of a given lead (440). The sub-threshold voltage pulse may be a bi-phasic voltage pulse or a mono-phasic voltage pulse. The first polarity may be either a positive or negative polarity. In response to delivery of the pulse, a first measurement of a first electrical parameter may be performed (442). Examples of the first electrical parameter that may be measured include a current value of the sub-threshold pulse delivered in the conductive pathway of the lead under test or a voltage value of the voltage induced in the conductive pathway of the lead under test. The measurement may be a unipolar measurement, i.e., electrode to device housing or a bipolar measurement through two electrodes of the lead. The first measurement of the electrical parameter subsequent to delivery of the sub-threshold pulse of the first polarity represents a first measurement cycle. The first measurement cycle may include one or more pulses being delivered with corresponding impedance measurements for each delivered pulse.

As noted above, when a sub-threshold pulse is delivered, an electrical parameter on the path is measured. To this end, sensing module 86 (FIG. 4) includes circuitry for obtaining samples of the electrical property on the path. Other examples of the circuitry are described in commonly assigned U.S. Pat. Nos. 5,755,742 and 7,233,825, both of which are incorporated herein by reference in their relevant parts. In the present embodiment of the disclosure, the sampling rate is programmable. For example, the peak-to-peak voltage across the heart may be sampled or the current through the electrode to housing can obtained for the measurement cycle.

Subsequently, a second measurement cycle may be performed with a second sub-threshold voltage pulse having a second polarity (444). Similar to the first sub-threshold voltage pulse, the second sub-threshold voltage pulse can be either a bi-phasic or mono-phasic pulse. However, it is preferred that the second sub-threshold voltage pulse of the second measurement cycle have a profile similar to that of the first measurement cycle in all respects with the exception of the polarity; the second polarity is opposite to that of the first polarity. In other words, if the first sub-threshold voltage pulse is a bi-phasic pulse with a positive polarity, then the second sub-threshold voltage pulse will be a bi-phasic pulse with a negative polarity and vice versa.

A measurement of a second electrical parameter may be performed following delivery of the second sub-threshold pulse (446). In one embodiment, the second electrical parameter measured following the second sub-threshold pulse may be the same parameter as the parameter measured following the first sub-threshold pulse at step 442. In another embodiment, yet another electrical parameter may be derived from each of the first measured electrical parameter and the second measured electrical parameter (448). For example, an impedance value may be derived from each of the electrical parameter obtained in the first measurement cycle and the electrical parameter obtained in the second measurement cycle. For ease of illustration, the electrical parameter derived from the first electrical parameter measured in the first measurement cycle will also be referred to as a first electrical parameter in the subsequent steps of the flow chart of FIG. 9. Similarly, the electrical parameter derived from the second electrical parameter measured in the second measurement cycle will also be referred to as a second electrical parameter in the subsequent steps of the flow chart.

The first electrical parameter and the second electrical parameter are compared to determine whether there is a difference in the values and if so whether the difference exceeds a predetermined threshold (450). The comparison of the electrical parameters for measurement of the difference between the values of the first electrical parameter and the second electrical parameter may be performed by electrical in the IMD 16 such as the processor 80 or dedicated circuitry such as impedance measurement circuitry. For example, a typical lead having an elongated electrode, such as electrode 62 of the present disclosure, will yield an impedance value of about 100 ohms from the positive polarity pulse test whereas the impedance from the negative polarity pulse test for the same electrode-bearing lead is about 60 ohms Therefore, the difference in polarity for a first and second measurement cycle for that example would be about 40 ohms.

In accordance with the embodiment of FIG. 9, if the difference between the electrical parameter obtained from the first measurement cycle and the electrical parameter obtained from the second measurement cycle exceeds a threshold value (452), the lead is determined to have an elongated electrode, such as electrode 62 described in FIGS. 5A-B, that has a first section comprising a first material and a second section comprising a second material that is different from the first material (454). Otherwise, the lead is determined not to have such an elongated electrode (456).

The above detailed description includes references to the accompanying drawings, which form a part of the detailed description. The drawings show, by way of illustration, specific embodiments in which the disclosure can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the terms "including" and "in which" are used as the plain-English equivalents of the respective terms "comprising" and "wherein." Also, in the document, the terms "including" and "comprising" are open-ended, that is, a system, device, article, or process that includes elements in addition to those listed after such a term in a claim are still deemed to fall within the scope of that claim. Moreover, in the document, the terms "first," "second," and "third," etc. are used merely as labels, and are not intended to impose numerical requirements on their objects, unless otherwise denoted.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), non-volatile random access memory (NVRAM), electrically erasable programmable read-only memory (EEPROM), FLASH memory, magnetic data storage media, optical data storage media, or the like.

The term "processor" or "processing circuitry" may generally refer to any of the foregoing logic circuitry, alone or in combination with other logic circuitry, or any other equivalent circuitry. Further, the present disclosure is not limited in scope to implantable medical devices including only a single processor but may be applicable to multiple-processor devices as well.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. It should also be understood that various changes can be made in the function and arrangement of elements without departing from the scope of the disclosure as set forth in the appended claims and the legal equivalents thereof.

What is claimed is:

1. An implantable medical system, comprising:
    an implantable medical device; and
    a medical electrical lead system coupled to the implantable medical device, including:
        a first electrode; and
        an alternate electrode having a first section and a second section,
            wherein the implantable medical device delivers therapy through a first vector including the first electrode and reconfigures the therapy for delivery through a second vector including the second section of the alternate electrode but not the first section of the alternate electrode in response to detecting a lead-related condition.

2. The implantable medical system of claim 1, wherein the first section is a proximal portion and the second section is a distal portion.

3. The implantable medical system of claim 1, wherein the second section comprises a first plurality of segments interspersed between the first section.

4. The implantable medical system of claim 1, further comprising:
    a sensing circuit; and
    an oversense reduction circuit coupled to the sensing circuit, wherein the oversense reduction circuit analyzes a composite signal detected through the second vector.

5. The implantable medical system of claim 1, wherein reconfiguring the therapy to be delivered by the implantable medical device comprises configuring the alternate electrode as a cathode.

6. The implantable medical system of claim 1, wherein reconfiguring the therapy to be delivered by the implantable medical device comprises switching from a first pacing mode to a second pacing mode in response to the lead condition.

7. The implantable medical system of claim 6, wherein the first pacing mode is a bipolar pacing configuration and the second pacing mode is a unipolar pacing configuration.

8. The implantable medical system of claim 1, wherein reconfiguring the therapy comprises modifying the stimulation profile of the pacing pulse.

9. The implantable medical system of claim 1, wherein reconfiguring the therapy comprises changing the energy threshold of the pacing pulse.

10. The implantable medical system of claim 1, further comprising a sensing circuit, wherein the sensing function is reconfigured in response to the lead related condition.

11. The implantable medical system of claim 10, wherein reconfiguring the sensing circuit comprises adjusting the filter characteristics of the sensing circuit responsive to detecting the lead-related condition.

12. The implantable medical system of claim 10, wherein reconfiguring the sensing circuit comprises adjusting at least one of a threshold and gain parameter of the sensing circuit responsive to detecting the lead-related condition.

13. The implantable medical system of claim 1, wherein the first section of the alternate electrode comprises a first material and the second section of the alternate electrode comprises a second material.

14. The implantable medical system of claim 1, wherein the alternate electrode is an elongated electrode.

15. The implantable medical system of claim 1, wherein the alternate electrode is constructed such that the first section comprises approximately 65% to approximately 95% of the total surface area of the alternate electrode.

16. The implantable medical system of claim 1, wherein the alternate electrode is constructed such that the first section comprises approximately 80% to approximately 90% of the total surface area of the alternate electrode.

17. The implantable medical system of claim 1, wherein the first electrode is coupled to a stimulation generator within the implantable medical device by a first conductor, and further wherein the alternate electrode is coupled to the stimulation generator within the implantable medical device by a second conductor to enable coupling of defibrillation energy to and through both the first and second sections of the alternate electrode.

18. An implantable medical system, comprising:
    an implantable medical device; and
    a medical electrical lead system coupled to the implantable medical device, comprising:
        a first electrode of a first pacing vector; and
        an alternate electrode having a first section and a second section of a cardioversion/defibrillation vector through which at least one of cardioversion and defibrillation therapy is deliverable, wherein the at least one of the cardioversion and defibrillation therapy is delivered through both the first and second sections of the alternate electrode,
    wherein the implantable medical device delivers therapy through the first pacing vector including the first electrode and reconfigures the therapy for delivery through a second pacing vector including the second section of the alternate electrode but not the first section of the alternate electrode in response to detecting a lead-related condition.

19. The implantable medical system of claim 18, wherein reconfiguring the therapy to be delivered by the implantable medical device comprises switching from a first pacing mode to a second pacing mode in response detecting a lead-related condition, wherein the first pacing mode is a bipolar pacing configuration and the second pacing mode is a unipolar pacing configuration.

20. The implantable medical system of claim 18, wherein the alternate electrode is constructed such that the first section comprises approximately 65% to approximately 95% of the total surface area of the alternate electrode.

* * * * *